United States Patent [19]

Trepanier

[11] 4,002,624
[45] Jan. 11, 1977

[54] SUBSTITUTED-3-THIO-1,2,4-TRIAZINES

[75] Inventor: Donald L. Trepanier, Midland, Mich.

[73] Assignee: The Dow Chemical Company, Midland, Mich.

[22] Filed: Jan. 26, 1976

[21] Appl. No.: 652,606

[52] U.S. Cl. .............................. 260/248 AS; 71/93; 424/249

[51] Int. Cl.$^2$ .............................. C07D 253/06

[58] Field of Search .............................. 260/248 AS

[56] References Cited

UNITED STATES PATENTS 3,966,715  6/1976  Westphal et al. .................. 260/248

Primary Examiner—John M. Ford
Attorney, Agent, or Firm—James W. Ambrosius

[57] ABSTRACT

The present invention is directed to novel 3-thio-1,2,4-triazines and addition salts thereof. The compounds are useful as herbicides, fungicides, insecticides, and antimicrobials.

5 Claims, No Drawings

SUBSTITUTED-3-THIO-1,2,4-TRIAZINES

SUMMARY OF THE INVENTION

The present invention is directed to thio-1,2,4-triazines having the general formula

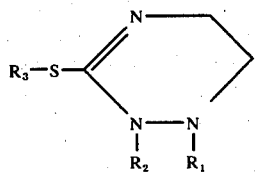

and the addition salts thereof wherein $R_1$ represents hydrogen or a lower alkyl group of from 1 to about 3 carbon atoms;

$R_2$ and $R_3$ independently represent benzyl, para-chlorobenzyl, diphenylmethyl, or 10,11-dihydro-5H-dibenzo(a,d)-cyclohepten-5-yl corresponding to the formula

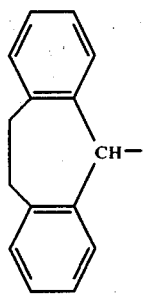

Operable addition salts of the above triazine compounds are those having anionic moieties which have no substantial detrimental effects upon the herbicidal, fungicidal, insecticidal, or antimicrobial activity of the compounds. Representative addition salts include acid addition salts formed by addition to the triazine compounds of inorganic acids such as hydrochloric, hydrobromic, sulfuric, and nitric acid or of organic acids such as acetic, lactic, maleic, succinic, fumaric, glutaric, citric, malic, sulfonic, tartaric acid, and the like.

The compounds of the present invention are crystalline solids which are of varying degrees of solubility in organic solvents such as ether, alcohols, chlorinated hydrocarbons, lower alkanes, and esters. The compounds of the present invention exhibit herbicidal, fungicidal, insecticidal, and antimicrobial activities; however a given compound may not show activity in all of the above mentioned areas.

BACKGROUND OF THE INVENTION

Triazinethiones have been reacted with a disubstituted ethane to give a thio-1,2,4-triazine, U.S. Pat. No. 3,641,019. The compounds of the present invention differ from those compounds described in the prior art in the substitutions on the triazine ring and particularly in the substitution attached to the sulfur connected to the ring at the 3-position.

A method for preparing crystalline azauridine using 3-thio-1,2,4-triazin-5(2H)-ones as starting materials is described in U.S. Pat. No. 3,135,737. Alkylthio-1,2,4-triazin-5-ones are also described in U.S. Pat. No. 3,910,909. Various 3-alkyl(or aryl)oxy-1,2,4-triazines are shown in U.S. Pat. Nos. 3,428,635 and 3,471,487.

DETAILED DESCRIPTION OF THE INVENTION

In general, the compounds of the present invention are prepared by reacting hydrazine or an alkylhydrazine with ethyleneimine to yield the corresponding 2-aminoethylthydrazine. See Trepanier et al., *Journal of Medicinal Chemistry*, 10, 228 (1967). This product in turn is reacted with carbon disulfide to prepare the corresponding triazinethione compound. The thio-as-triazine compounds of the present invention are obtained by reacting a triazinethione intermediate with an aryl halide. In such procedures hydrazine or an alkylhydrazine is reacted with ethyleneimine in the presence of a catalytic amount of ammonium chloride as shown below.

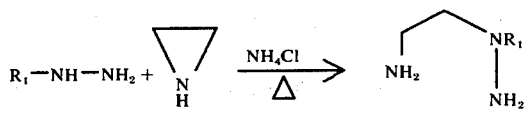

wherein $R_1$ and $R_2$ have the same significance as described hereinbefore.

The reaction mixture usually is heated at the boiling temperature for about 24 hours. Thereafter, excess hydrazine is distilled off and the resulting 2-aminoethylhydrazine product separated by fractional distillation.

Additional substitution on the 2-aminoethyl hydrazine to provide a compound with an $R_2$ group may be accomplished through the reaction of this compound with a selected aldehyde, followed by hydrogenation as illustrated directly hereinafter.

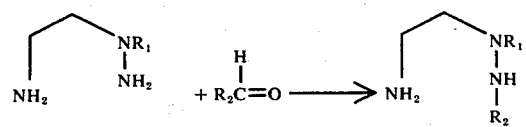

Contacting the 2-aminoethylhydrazine with carbon disulfide results in the preparation of the corresponding triazinethione; U.S. Pat. No. 3,732,219. In a convenient procedure, the 2-aminoethylhydrazine is dispersed in an inert organic liquid as reaction medium and the carbon disulfide is added slowly to the mixture with stirring as illustrated below.

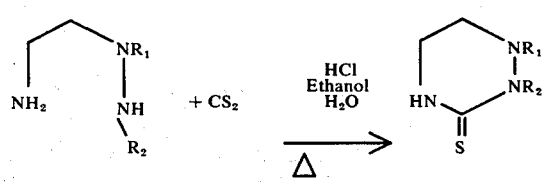

The thio-as-triazine of the present invention is prepared by reacting the triazinethione intermediate made by the process described above with an aryl halide. The reaction may be represented as follows:

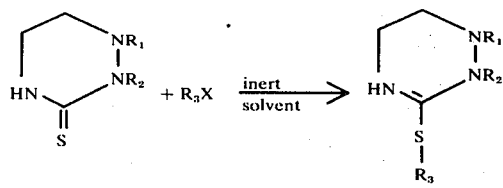

The reaction proceeds when the reactants are contacted and mixed, preferably in an inert reaction medium. Representative inert organic liquids which can be employed as reaction media include lower-alkanols of 1 to 4 carbon atoms, acetone, glycols of the ethylene, propylene and trimethylene series, dimethylformamide, dimethylsulfoxide and methylene chloride.

EXAMPLE 1

Preparation of
2-Benzyl-3-(benzylthio)-1,2,5,6-tetrahydro-1-methyl-1,2,4-triazine Seven grams of tetrahydro-1-methyl-2-(phenylmethyl)-1,2,4-triazine-3(2H)-thione was dissolved in 30 ml. of dimethyl formamide. Three grams of finely ground potassium carbonate ($K_2CO_3$) was added to the solution. Benzyl bromide (5.43 grams) was added in several additions at room temperature. The mixture was heated to 60°–65° C and held at that temperature for 2 hours. The mixture was chilled and diluted with additional $K_2CO_3$ (10 g.) and water (200 ml). The product was extracted with trichloromethane and washed with brine. The mixture was dried with magnesium sulfate. The mixture was diluted with ethyl ether and the insoluble particles filtered off. The filtrate was heated to 35° C to concentrate the solution. Upon chilling 2-benzyl-3-(benzylthio)-1,2,5,6-tetrahydro-1-methyl-1,2,4-triazine crystallized from the liquid reaction mass. This product was recrystallized from isopropanol-hexane. The product was found to have a melting point at 45° C. The structure was confirmed by IR, NMR and elemental analysis.

Using the general procedure described above the following thio-1,2,4-triazines were prepared.

The compounds 2-benzyl-3-(benzylthio)-1,2,5,6-tetrahydro-1-as-triazine (Example 1) and 2-[10,11-dihydro-5H-dibenzo(a,d)-cyclohepten-5-yl]-3-[(10,11-dihydro-5H-dibenzo(a,d)cyclohepten-5-yl)thio]-1,2,5,6-as-triazine (Example 3, Table I) have been shown to be effective herbicides in the control and killing of pigweeds and crabgrass when used in a concentration of 20 pounds per acre.

The compound 2-benzyl-3-(benzylthio)-1,2,5,6-tetrahydro-1-1,2,4-triazine (Example 1) has proven to be an effective fungicide and antimicrobial when used in a concentration of 500 parts per million. Species against which the compound was found to be effective include *Staphylococcus aureus*, *Candida albicans*, *Trichophton mentagrophytes*, *Bacillus subtilis*, *Aspergillus terreus*, *Candida pelliculosa*, *Pullularia pullulans*, *Salmonella typhosa*, *Mycobacterium phlei*, *Rhizopus nigricans*, *Ceratocystis ips*, *Cephaloascus fragans*, and *Trichoderm* sp. Madison sp-42.

The compound 2-(p-chlorobenzyl)-3-[(p-chlorobenzyl)thio]-1,4,5,6-tetrahydro-1,2,4-triazine (Example 4, Table I) was found to be an effective insecticide and arachicide. The compound will control and kill cabbage looper and two spotted spider mites at a concentration of 400 parts per million. At a concentration of 12 parts per million, the compound was found to control and kill the Southern house mosquito.

The compound 2-(diphenylmethyl)-3-[(diphenylmethyl)-thio]-1,2,5,6-tetrahydro-1,2,4-triazine (Example 2, Table I) was found to be effective in the controlling and killing of fungus-leaf rust in wheat when used in a concentration of 25 parts per million.

I claim:
1. A compound of the formula

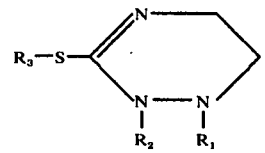

wherein
$R_1$ represents hydrogen or a lower alkyl group of from 1 to about 3 carbon atoms,
$R_2$ and $R_3$ independently represent benzyl, para-chlorobenzyl, diphenylmethyl, and 10,11-dihydro-5H-dibenzo(a,d)-cyclohepten-5-yl and the addition salts thereof.

2. The compound of claim 1 which is 2-benzyl-3-(benzylthio)-1,2,5,6-tetrahydro-1-1,2,4-triazine.

TABLE I

Thio-1,2,4-triazines corresponding to the formula:

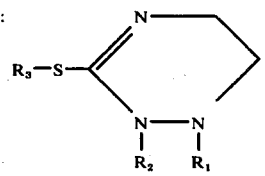

| Example | $R_1$ | $R_2$ | $R_3$ | Mp, °C | Recrystallization Solvent | Formula |
|---|---|---|---|---|---|---|
| 2 | H | diphenylmethyl | diphenylmethyl | 121–122 | isopropanol | $C_{29}H_{27}N_3S$ |
| 3 | H | (10,11-dihydro-5H-dibenzo(a,d)cyclohepten-5-yl) | (10,11-dihydro-5H-dibenzo(a,d)cyclohepten-5-yl) | 166–168 | isopropanol | $C_{33}H_{31}N_3S$ |
| 4 | H | p-chlorobenzyl | p-chlorobenzyl | 190–191 | ethanol-diethylether | $C_{17}H_{17}Cl_2N_3S$ |

3. The compound of claim 1 which is 2-(diphenylmethyl)-3-[(diphenylmethyl)thio]-1,2,5,6-tetrahydro-1,2,4-triazine.

4. The compound of claim 1 which is 2(10,11-dihydro-5H-dibenzo(a,d)-cyclohepten-5-yl)-3-((10,11-dihydro-5H-dibenzo(a,d)-cyclohepten-5-yl)thio)-1,2,5,6-tetrahydro-1,2,4-triazine.

5. The compound of claim 1 which is 2-(p-chlorobenzyl)-3-((p-chlorobenzyl)thio)-1,4,5,6-tetrahydro-1,2,4-triazine.

* * * * *